(12) United States Patent
McHale et al.

(10) Patent No.: US 9,724,542 B2
(45) Date of Patent: *Aug. 8, 2017

(54) REMINERALIZING AND DESENSITIZING COMPOSITIONS, TREATMENTS AND METHODS OF MANUFACTURE

(71) Applicant: Premier Dental Products Company, Plymouth Meeting, PA (US)

(72) Inventors: William A. McHale, Collegeville, PA (US); Dale G. Brown, Wharton, TX (US)

(73) Assignee: Premier Dental Products Company, Plymouth Meeting, PA (US)

( * ) Notice: Subject to any disclaimer, the term of this patent is extended or adjusted under 35 U.S.C. 154(b) by 45 days.

This patent is subject to a terminal disclaimer.

(21) Appl. No.: 13/651,044

(22) Filed: Oct. 12, 2012

(65) Prior Publication Data

US 2014/0105941 A1 Apr. 17, 2014

(51) Int. Cl.

| | | |
|---|---|---|
| *A61Q 11/00* | (2006.01) | |
| *A61K 9/00* | (2006.01) | |
| *A61K 8/90* | (2006.01) | |
| *A61K 8/06* | (2006.01) | |
| *A61K 9/107* | (2006.01) | |

(52) U.S. Cl.
CPC ............. *A61Q 11/00* (2013.01); *A61K 8/062* (2013.01); *A61K 8/90* (2013.01); *A61K 9/006* (2013.01); *A61K 9/0063* (2013.01); *A61K 9/107* (2013.01); *A61K 2800/31* (2013.01)

(58) Field of Classification Search
CPC .......... A61Q 11/00; A61K 9/006; A61K 8/90; A61K 8/062; A61K 9/0063; A61K 2800/31; A61K 9/107
See application file for complete search history.

(56) References Cited

U.S. PATENT DOCUMENTS

| | | | |
|---|---|---|---|
| 3,442,842 | A | 5/1969 | Bonin |
| 4,296,096 | A | 10/1981 | Pierce |
| 4,647,451 | A | 3/1987 | Piechota |
| 4,652,441 | A | 3/1987 | Okada et al. |
| 4,711,782 | A | 12/1987 | Okada et al. |
| 4,911,927 | A | 3/1990 | Hill et al. |

(Continued)

FOREIGN PATENT DOCUMENTS

| | | |
|---|---|---|
| CN | 1093058 A | 10/1994 |
| CN | 1190342 A | 8/1998 |

(Continued)

OTHER PUBLICATIONS

Attin, T., et al., "Deposition of fluoride on enamel surfaces released from varnishes is limited to vicinity of fluoridation site", Clin Oral Investig, vol. 11, pp. 83-88, 2007.

(Continued)

*Primary Examiner* — Trevor Love
(74) *Attorney, Agent, or Firm* — Cozen O'Connor (57) ABSTRACT

Improved remineralizing and desensitizing compositions containing remineralizing ingredients in aqueous-free emulsions that, in the presence of saliva, form mucoadhesive gels substantive to tooth surfaces; wherein the gels are dissolved by saliva gradually releasing remineralizing ingredients onto tooth surfaces, treatments with these compositions and methods of manufacture.

24 Claims, 7 Drawing Sheets

(56) References Cited

U.S. PATENT DOCUMENTS

| | | |
|---|---|---|
| 4,942,034 A | 7/1990 | Hill et al. |
| 5,009,881 A | 4/1991 | Hill et al. |
| 5,032,387 A | 7/1991 | Hill et al. |
| 5,037,639 A | 8/1991 | Tung |
| 5,057,306 A | 10/1991 | Hill et al. |
| 5,057,307 A | 10/1991 | Hill et al. |
| 5,057,309 A | 10/1991 | Hill et al. |
| 5,098,711 A | 3/1992 | Hill et al. |
| 5,165,913 A | 11/1992 | Hill et al. |
| 5,268,167 A * | 12/1993 | Tung ........................ 424/52 |
| 5,427,768 A | 6/1995 | Tung |
| 5,437,857 A | 8/1995 | Tung |
| 5,460,803 A | 10/1995 | Tung |
| 5,538,667 A | 7/1996 | Hill et al. |
| 5,562,895 A | 10/1996 | Tung |
| 5,651,959 A | 7/1997 | Hill et al. |
| 5,665,374 A | 9/1997 | Hill et al. |
| 5,665,382 A | 9/1997 | Grinstaff et al. |
| 5,711,935 A | 1/1998 | Hill et al. |
| 5,925,595 A | 7/1999 | Seitz et al. |
| 5,952,317 A | 9/1999 | Deluca et al. |
| 6,054,119 A | 4/2000 | Hurme et al. |
| 6,086,373 A | 7/2000 | Schiff et al. |
| 6,159,449 A | 12/2000 | Winston et al. |
| 6,184,255 B1 | 2/2001 | Mae et al. |
| 6,441,050 B1 | 8/2002 | Chopra |
| 6,534,091 B1 | 3/2003 | Garces Garces et al. |
| 6,545,077 B2 | 4/2003 | Hill et al. |
| 6,569,408 B1 | 5/2003 | Yue et al. |
| 6,575,176 B1 | 6/2003 | Hill et al. |
| 6,740,338 B1 | 5/2004 | Chopra |
| 7,017,591 B2 | 3/2006 | Brown et al. |
| 7,025,986 B2 | 4/2006 | Brown et al. |
| 7,152,611 B2 | 12/2006 | Brown et al. |
| 7,303,921 B2 | 12/2007 | Littarru et al. |
| 7,897,169 B2 | 3/2011 | Ueda et al. |
| 2002/0090398 A1 | 7/2002 | Dunn et al. |
| 2003/0165442 A1 | 9/2003 | Baig et al. |
| 2003/0198604 A1 | 10/2003 | Lawlor |
| 2004/0057908 A1 | 3/2004 | Bowen |
| 2004/0126335 A1 | 7/2004 | Faller et al. |
| 2004/0258634 A1 | 12/2004 | Cazor et al. |
| 2005/0196440 A1 | 9/2005 | Masters et al. |
| 2006/0093558 A1 | 5/2006 | Lin et al. |
| 2006/0120980 A1 | 6/2006 | Eberl |
| 2006/0177384 A1 | 8/2006 | Brown |
| 2006/0286046 A1 | 12/2006 | Haber |
| 2007/0190090 A1* | 8/2007 | Brown .......................... 424/401 |
| 2008/0039434 A1 | 2/2008 | Colli |
| 2008/0044454 A1 | 2/2008 | Yang et al. |
| 2008/0050408 A1 | 2/2008 | Hayman et al. |
| 2008/0069781 A1 | 3/2008 | Neuberger |
| 2008/0095719 A1 | 4/2008 | Herrmann et al. |
| 2008/0152598 A1 | 6/2008 | Basic |
| 2008/0152599 A1 | 6/2008 | Brignoli et al. |
| 2008/0175918 A1 | 7/2008 | Laulicht |
| 2008/0226710 A1 | 9/2008 | Fantuzzi |
| 2008/0247973 A1 | 10/2008 | Baig et al. |
| 2008/0286214 A1 | 11/2008 | Brown et al. |
| 2008/0295960 A1 | 12/2008 | Schalau, II et al. |
| 2009/0042161 A1 | 2/2009 | Jodaikin et al. |
| 2009/0087501 A1 | 4/2009 | Cummins |
| 2009/0188520 A1 | 7/2009 | Brown |
| 2009/0232752 A1 | 9/2009 | Carson et al. |
| 2009/0280078 A1 | 11/2009 | Belfer |
| 2010/0135918 A1 | 6/2010 | Kim et al. |
| 2010/0330003 A1 | 12/2010 | Robinson et al. |
| 2011/0014136 A1 | 1/2011 | Kohli et al. |
| 2011/0104052 A1 | 5/2011 | Barnett et al. |
| 2011/0118217 A1 | 5/2011 | Gudmundsson et al. |
| 2012/0021031 A1 | 1/2012 | Chopra et al. |
| 2012/0064136 A1 | 3/2012 | Baker et al. |
| 2012/0129135 A1 | 5/2012 | Yang et al. |
| 2012/0171128 A1 | 7/2012 | Ramirez |
| 2012/0207686 A1 | 8/2012 | Fruge et al. |
| 2012/0245080 A1 | 9/2012 | Goolsbee et al. |
| 2013/0344120 A1 | 12/2013 | Scott et al. |

FOREIGN PATENT DOCUMENTS

| | | |
|---|---|---|
| CN | 101056606 A | 10/2007 |
| EP | 0 559 262 | 4/1996 |
| EP | 0868903 A2 | 10/1998 |
| WO | 9511746 A1 | 5/1995 |
| WO | 9639116 A1 | 12/1996 |
| WO | WO 01/26577 | 4/2001 |
| WO | 03068173 A1 | 8/2003 |
| WO | 2007036802 A2 | 4/2007 |
| WO | 2007092811 A2 | 8/2007 |
| WO | 2007099398 A1 | 9/2007 |
| WO | 2008047882 A1 | 4/2008 |
| WO | 2009080022 A1 | 7/2009 |
| WO | 2010010394 A2 | 1/2010 |
| WO | WO 2013/039906 | 3/2013 |
| WO | WO 2014/001132 | 1/2014 |

OTHER PUBLICATIONS

Belran-Aguillar, E.D., et al., "Fluoride varnishes: A review of their clinical use, cariostatic mechanism, efficacy and safety", JADA, vol. 131, pp. 589-594, 2000.

Caslavska, V., et al., "CaF2 in Enamel Biopsies 6 Weeks and 18 Months after Fluoride Treatment", Caries Res, vol. 25, pp. 21-26, 1991.

Chow, L.C., et al., "Apatitic fluoride increase in enamel from a topical treatment involving intermediate CaHPO4.2H20 formation, an in vivo study", Caries Res, vol. 15, pp. 369-376, 1981.

Christoffersen, J., et al., "Kinetics of dissolution and growth of calcium fluoride and effects of phosphate", Acta Odontol Scand, vol. 46, No. 6, pp. 325-336, 1988.

Crall, J.J., et al., "Enamel fluoride retention after DCPD and APF application and prolonged exposure to fluoride in vitro", J Dent Res, vol. 65, No. 3, pp. 387-389, Mar. 1986.

Cruz, R., et al., "Uptake of KOH-soluble and KOH-insoluble fluoride in sound human enamel after topical application of a fluoride varnish (Duraphat) or a neutral 2% NaF solution in vitro", Scand J Dent Res., vol. 100, No. 3, pp. 154-158, 1992.

Dijkman, A.G., et al., "In vivo investigation on the fluoride content in and on human enamel after topical applications", Caries Res, vol. 17, pp. 392-402, 1983.

Dudev, T., et al., "Monodentate versus bidentate carboxylate binding in magnesium and calcium proteins: what are the basic principles?", J. Phys. Chem. B., vol. 108, pp. 4546-4557, 2004.

Featherstone, J.D.B., "Prevention and reversal of dental caries: role of low level fluoride", Community Dent Oral Epidemiol, vol. 27, pp. 31-40, 1999.

Featherstone, J.D.B., "The Science and Practice of Caries Prevention", Journal of the American Dental Association, vol. 131, pp. 887-899, 2000.

Helfenstein, U., et al., "Fluoride varnishes (Duraphat): A meta-analysis", Community Dent Oral Epidemiol, vol. 22, pp. 1-5, 1994.

Hong, Y.C., et al., "Enhanced fluoride uptake from mouthrinses", J Dent Res, vol. 64, pp. 82-84, 1985.

Koch, G., K.G., et al., "Effect of 250 and 1000 ppm fluoride dentifrice on caries; a three-year clinical study", Swed Dent J, vol. 6, pp. 233-238, 1982.

Margolis, H.C., et al., "Physicochemical perspectives on the cariostatic mechanisms of systemic and topical fluorides", J Dent Res, vol. 69 (Special Issue), pp. 606-613, 1990.

Marinho, V.C., et al., "Fluoride varnishes for preventing dental caries in children and adolescents" (review), Cochrane Database Syst Rev, (3):CD002279, 2002.

Mitropoulos, C.M., et al., "Relative efficacy of dentifrices containing 250 or 1000 ppm F—in preventing dental caries report of a 32-month clinical trial", Community Dent Health, vol. 1, pp. 193-200, 1984.

(56) References Cited

OTHER PUBLICATIONS

Øgaard, B., et al., "Relative cariostatic effects of KOH-soluble and KOH-insoluble fluoride in situ", J. Dent Res, vol. 69, pp. 1505-1507, 1990.
Øgaard, B., "CaF2 Formation: Cariostatic Properties and Factors of Enhancing the Effect", Caries Res., vol. 35 (Suppl 1), pp. 40-44, 2001.
Pendrys, D.G., "Risk of Enamel Fluorosis in Nonfluoridated and Optimally Fluoridated Populations: Considerations for the Dental Professional", Journal of the American Dental Association, vol. 131, No. 6, pp. 746-755, 2000.
Ripa, L.W., "A critique of topical fluoride methods (dentifrices, mouthrinses, operator-, and self-applied gels) in an era of decreased caries and increased fluorosis prevalence", J Public Health Dent., Winter, vol. 51, No. 1, pp. 23-41, 1991.
Rolla, G., et al., "Concentration of fluoride in plaque a possible mechanism", Scand. J. Dent. Res., vol. 85, pp. 149-151, 1977.
Rose, R.K., et al., "A quantitative study of calcium binding and aggregation in selected oral bacteria", J Dent Res, vol. 72, pp. 78-84, 1993.
Schaeken, M.J., et al., "Effects of fluoride and chlorhexidine on the microflora of dental root surfaces and the progression of root-surface caries", J Dent Res, vol. 70, No. 2, pp. 150-153, 1991.
Schemehorn, B.R., et al., "Comparison of Fluoride Uptake into Tooth Enamel from Two Fluoride Varnishes Containing Different Calcium Phosphate Sources", ACP Technology, The Journal of Clinical Dentistry, vol. XXII, No. 2, pp. 51-54, 2011.
Schreiber, C.T., et al., "Effects of rinses with an acidic calcium phosphate solution on fluoride uptake, caries and in situ plaque pH in rats", J Dent Res, vol. 67, pp. 959-963, 1988.
Stookey, G.K., "Critical evaluation of the composition and use of topical fluorides", J Dent Res, vol. 69 (Spec Iss), pp. 805-812, 1990.
Tan, H.P., et al., "A randomized trial on root caries prevention in elders", J Dent Res, vol. 89, No. 10, pp. 1086-1090, 2010.
ten Cate, J.M., "Review on Fluoride with special emphasis on calcium fluoride mechanisms in caries prevention", Eur. J. Oral Sci., vol. 105 (5 pt 2), pp. 461-465, Oct. 1997.
Tewari, A., et al., "Comparative evaluation of the role of NaF, APF, and Duraphat topical fluoride applications in the prevention of dental caries: A 2½ year study", J Indian Soc Pedod Prev Dent, vol. 8, pp. 28-36, 1990.
Tung, M.S., et al., "Dental applications of amorphous calcium phosphates", J. Clin Dent, vol. 10, pp. 1-6, 1999.
Turner, D., et al., "The Interaction of Stannous Fluoride with Synthetic Hydroxyapatite: Modeling the Anticaries Effect", Ceramics—Silikaty, vol. 57, No. 1, pp. 1-6, 2013.
Vaikuntam, J., "Fluoride varnishes: should we be using them?", Pediatr Dent, vol. 22, pp. 513-516, 2000.
Vogel, G.L., et. al., "Salivary fluoride from fluoride dentifrices or rinses after use of a calcium pre-rinse or calcium dentifrice", Caries Res., vol. 40, pp. 449-454, 2006.
Vogel, G.L., et. al., "Calcium Pre-Rinse Greatly Increases Overnight Salivary Fluoride after a 228 ppm Fluoride Rinse", Caries Res., vol. 42, No. 5, pp. 401-404, Sep. 2008.
Vogel, G.L., et. al., "Ca Pre-Rinse Greatly Increases Plaque and Plaque Ffluid F", J. Dent. Res., vol. 87, No. 5, pp. 466-469, May 2008.
Vogel, G.L., et al., in "No Calcium-Fluoride-Like Deposits Detected in Plaque shortly after a Sodium Fluoride Mouthrinse", Caries Res., vol. 44, No. 2, pp. 108-115, 2010.
Walton, J.G., et al., "Textbook of Dental Pharmacology and Therapeutics", Oxford University Press 1994, pp. 149 and 154.
Warren, J.J., et al., "A review of fluoride dentifrice related to dental fluorosis", Pediatr. Dent., vol. 21, No. 4, pp. 265-271, Jul.-Aug. 1999.
Zero, D.T., "Dentifrices, mouthwashes, and remineralization/caries arrestment strategies", BMC Oral Health, vol. 6 (Suppl 1), No. 59, pp. 1-13, 2006.
Search Report and Written Opinion dated Jul. 2, 2015 which issued in International Patent Application No. PCT/US15/25375.
Search Report and Written Opinion dated Jul. 10, 2015 which issued in International Patent Application No. PCT/US15/25385.
Search Report and Written Opinion dated Jul. 2, 2015 which issued in International Patent Application No. PCT/US15/25391.
Search Report and Written Opinion dated Jul. 2, 2015 which issued in International Patent Application No. PCT/US15/25396.
International Search Report issued in International Application No. PCT/US2013/064504 on Apr. 21, 2014.
Wu, L. C., et al., "Anti-inflammatory effect of spilanthol from Spilanthes acmella on murine macrophage by down-regulating LPS-induced inflammatory mediators", J. Agric. Food Chem., vol. 56, No. 7, pp. 2341-2349, Apr. 9, 2008 (Apr. 9, 2008), Abstract.
Barry, R., "The Power of Ubiquinol", The Key to Energy, Vitality, and a Healthy Heart, Chapter 4, Studies and Research: The Health Benefits of Ubiquinol, pp. 21-25, 2010.
Bashutski, J.D., et al., "The Impact of Vitamin D Status on Periodontal Surgery Outcomes", J. Dent. Res., vol. 90, No. 8, pp. 1007-1012, 2011.
Chantal, J., et al., "The coming of age of 1,25-dihydroxyvitamin D3 analogs as immunomodulatory agents", Trends Mol Med., vol. 8, No. 4, pp. 174-179, 2002.
Charig, A. et al., "CE3 Enamel Mineralization by Calcium-containing Bicarbonate Toothpastes: Assessment by Various Techniques", Compendium, vol. 25, No. 9 (Suppl 1), pp. 15-31, Sep. 2004.
Diamond, G., et al., "Host defense peptides in the oral cavity and the lung: similarities and differences", J. Dent. Res., vol. 87, No. 10, pp. 915-927, 2008.
Dietrich, T., et al., Association between serum concentrations of 25-hydroxyvitamin D and gingival inflammation1'2'3', Am. J. Clin. Nutr., vol. 82, No. 3, pp. 575-580, 2005.
Dimeloe, S., et al., "Regulatory T cells, inflammation and the allergic response—The role of glucocorticoids and Vitamin D", Journal of Steroid Biochemistry & Molecular Biology, vol. 120, Issues 2-3, pp. 86-95, 2010.
Ernster, L., et al., "Ubiquinol: an endogenous antioxidant in aerobic organisms", Clin Investig, vol. 71, (8 Suppl), pp. S60-S65, 1993.
Folkers, K., "A critique of 25 years of research which culminated in the successful therapy of periodontal disease with coenzyme Q10", J. Dent. Health, vol. 42, pp. 258-263, 1992.
Garcia, M., et al., "One-Year Effects of Vitamin D and Calcium Supplementation on Chronic Periodontitis", Journal of Periodontology, vol. 82, No. 1, pp. 25-32, 2011.
Gombart, A.F., "The vitamin D-antimicrobial peptide pathway and its role in protection against infection", Future Microbiology, vol. 4, No. 9, pp. 1151-1165, 2009.
Hanioka, T., et al., "Therapy with Coenzyme Q10 for Patients with Periodontal Disease: 2. Effect of Coenzyme Q10 on the Immune System", Journal of Dental Health, vol. 43, pp. 667-672, 1993.
Hanioka, T., et al., "Effect of Topical Application of Coenzyme Q10 on Adult Periodontitis", Molec. Aspects of Med., vol. 85 (Supplement), pp. S241-S248, 1994.
Hansdottir, S., et al., "Vitamin D Decreases Respiratory Syncytial Virus Induction of NF-κB—Linked Chemokines and Cytokines in Airway Epithelium While Maintaining the Antiviral State", The Journal of Immunology, vol. 184, No. 2, pp. 965-974, 2010.
Hewison, M., "Review: Vitamin D and the intracrinology of innate immunity", Molecular and Cellular Endocrinology, vol. 321, No. 2, pp. 103-111, 2010.
Holick, M.F., "Vitamin D Deficiency", New England Journal of Medicine, vol. 357, pp. 266-281, 2007.
Holick, M.F., "Vitamin D Status: Measurement, Interpretation, and Clinical Application", Annals of Epidemiology, vol. 19, No. 2, pp. 73-78, 2009.
International Search Report and Written Opinion dated Oct. 12, 2012 which issued in International Patent Application No. PCT/US2013/064358.
Kamen, D.L., et al., "Vitamin D and molecular actions on the immune system: modulation of innate and autoimmunity", J. Mol. Med., vol. 88, pp. 441-450, 2010.
Lei, et al., In Vitro Degradation of Novel Bioactive Polycaprolactone-20% Tricalcium Phosphate Composite Scaffolds for Bone Engineering, Materials and Science and Engineering, vol. 27, issue 2, Mar. 2007.

(56) References Cited

OTHER PUBLICATIONS

Litkowski et al., "CE4, Intraoral Evaluation of Mineralization of Cosmetic Defects by a Toothpaste Containing Calcium, Fluoride, and Sodium Bicarbonate", Compendium, vol. 25, No. 9, Sep. 2004.
Littarru, G.P., et al., "Deficiency of coenzyme Q10 in gingival tissue from patients wit periodontal disease", Proc. Natl. Acad. Science USA, vol. 68, No. 10, pp. 2332-2335, Oct. 1971.
Lowenstein et al., "Vaterite: A Mineraliztion Product of the Hard Tissues of Marine Organism (*Ascidiacea*)" Science, vol. 188, pp. 363-365, 1972.
McRee, Jr., J.T., et al., "Therapy with coenzyme Q10 for patients with periodontal disease: 1. Effect of Coenzyme Q10 on Subgingival Microorganisms", Journal of Dental Health, vol. 43, pp. 659-666, 1993.
McMahon, L., et al., "Vitamin D-Mediated Induction of Innate Immunity in Gingival Epithelial Cells", Infection and Immunity, vol. 79, pp. 2250-2256, 2011.
Miley, D.D., et al., "Cross-sectional study of vitamin D and calcium supplementation effects on chronic periodontitis", J. Periodontol., vol. 80, No. 9, pp. 1433-1439, Sep. 2009.
Mitropoulos, C.M., et al., "Relative efficacy of dentifrices containing 250 or 1000 ppm F—in preventing dental caries-report of a 32-month clinical trial", Community Dent Health, vol. 1, pp. 193-200, 1984.
Mohammed, N.R., et al., "Effects of Fluoride on in vitro Enamel Demineralization Analyzed by 19F MAS-NMR", Caries Res, vol. 47, pp. 421-428, 2013.
Nakamura, R., et al., "Deficiency of Coenzyme Q in Gingiva of Patients with Dental Disease", Internat. J. Vit. Nutr. Res., vol. 43, pp. 85-92, 1973.
Nizet, V., et al., "Cathelicidins and Innate Defense Against Invasive Bacterial Infection", Scandinavian Journal of Infectious Diseases, vol. 35, No. 9, pp. 670-676, 2003.
Oral Health: Different Ages/Different Stages: Birth to 12 12 Years, Ontario, Mar. 2009, pp. 1-24.
Park, K.S., et al., "The short vitamin D receptor is associated with increased risk for generalized aggressive periodontitis", Journal of Clinical Periodontology, vol. 33, No. 8, pp. 524-528, 2006.
Roveri, N., et al., "Surface Enamel Remineralization: Biomimetic Apatite Nanocrystals and Fluoride Ions Different Effects", Journal of Nanomaterials, vol. 2009, Article ID 746383, 9 pages.
Schmelzer, C., et al., "In vitro effects of the reduced form of coenzyme Q10 on secretion levels of TNF-$\alpha$ and chemokines in response to LPS in the human monocytic cell line THP-1," Journal of Clinical Biochemistry and Nutrition, vol. 44, No. 1, pp. 62-66, 2009.
Sun, J., "Vitamin D and mucosal immune function", Current Opinion in Gastroenterology,vol. 26, No. 6, pp. 591-594, Nov. 2010.
Tang, P.H., et al., "HPLC Analysis of Reduced and Oxidized Coenzyme Q10 in Human Plasma", Clinical Chemistry, vol. 47, No. 2, pp. 256-265, 2001.
ten Cate, J.M., "Current Concepts on the Theories of the Mechanism of Action of Fluoride", Academic Centre for Dentistry Amsterdam (ACTA), Odontol of Cariology, Endodontology Pedodontology, Amsterdam, The Netherlands, ACTA Odoritol Scand, vol. 57, pp. 325-329, 1999.
Tung, M.S., et al., "CE2, Amorphous Calcium Phosphates for Tooth Mineralization", Compendium, vol. 25, No. 9 (Suppl 1), pp. 9-13, Sep. 2004.
Vieth, R., et al., "Efficacy and safety of vitamin D3 intake exceeding the lowest observed adverse effect level", Am J Clin Nutr, vol. 73, No. 2, pp. 288-294, Feb. 2001.
Wang, X.L., et al., "Cosupplementation with vitamin E and coenzyme Q10 reduces circulating markers of inflammation in baboons1-3", Am. J. Clin. Nutr., vol. 80, No. 3, pp. 649-655, Sep. 2004.
Wang, C., et al., "Association Between Vitamin D Receptor Gene Polymorphisms and Severe Chronic Periodontitis in a Chinese Population", Journal of Periodontology, vol. 80, No. 4, pp. 603-608, 2009.
Wilkinson, E.G., et al., "Bioenergetics in clinical medicine. II. Adjunctive treatment with coenzyme Q10 in periodontal therapy", Res. Com. Chem. ath. Pharm, vol. 12, No. 1, p. 111-123, 1975.
Wilkinson, E.G., et al., "Bioenergetics in clinical medicine. VI. Adjunctive treatment of periodontal disease with coenzyme Q10", Res. Com. Chem. Path. Pharm., vol. 14, No. 4, pp. 715-719, 1976.
Xu, H.H.U., et al., "Strong Nanocomposites with Ca PO4, and F Release for Caries Inhibition", J. Dent Res, vol. 89, No. 1, pp. 19-28, 2010.
International Preliminary Report on Patentability dated Oct. 20, 2016, issued in corresponding application No. PCT/US2015/025375.

\* cited by examiner

REMINERALIZING AND DESENSITIZING COMPOSITIONS, TREATMENTS AND METHODS OF MANUFACTURE

FIELD OF THE INVENTION

The present invention is directed to an advance in remineralizing and desensitizing compositions, whereby the remineralizing and desensitizing ingredients are substantive to tooth surfaces, thereby extending the remineralizing or desensitizing process and corresponding remineralizing or desensitizing effectiveness. Key remineralizing and desensitizing ingredients include: various fluorides, amorphous calcium phosphate (ACPF) mixtures, bioglass (NovaMin®), tricalcium phosphate fluoride mixtures, etc.

BACKGROUND OF THE INVENTION

ACPF remineralizing/desensitizing compositions and their remineralizing/desensitizing effects are a preferred embodiment of the present invention. ACPF mixtures are presently marketed under the ENAMEL PRO® brand.

Remineralizing/desensitizing compositions marketed commercially that are useful in the present invention include: ACPF mixtures, bioglass compositions marketed under the trademark, NovaMin®; tricalcium phosphate fluoride mixtures marketed under the trademark, Clinpro™; various fluoride compositions marketed under trademarks including: GELKAM®, Prevident®, Periogard®, etc.

"Washout" of remineralizing/desensitizing ingredients from tooth surfaces by saliva flow, eventually controls the effective residence time of various commercial, remineralizing/desensitizing ingredients on tooth surfaces, controlling the remineralizing/desensitizing effectiveness of the various remineralizing/desensitizing ingredients presently marketed and/or described in the prior art. To improve remineralizing/desensitizing effectiveness, commercial, professionally prescribed, fluoride remineralizing/desensitizing compositions resort to high levels of fluoride, i.e. 5000 ppm for Rx toothpastes, gels and rinses and to approximately 19,000 ppm fluoride for "in-chair" professionally applied varnishes. In contrast, standard OTC remineralizing/desensitizing toothpastes, etc., contain up to 1500 ppm fluoride under the FDA's Fluoride Monograph.

There is a need to improve remineralizing/desensitizing effectiveness for professional oral care treatments and for OTC products for patient use, while reducing the risk associated with exposure to high fluoride levels. For the balance of this specification, the term "remineralizing" is used to describe both "remineralizing and desensitizing" treatments.

OBJECTS OF THE PRESENT INVENTION

An object of the present invention is to improve the remineralizing effectiveness of various remineralizing ingredients including: ACPF mixtures, bioglass, tricalcium phosphate, fluoride mixtures and various fluorides in: gels, prophy pastes, rinses, chewing gums, interproximal devices, etc.

Another object of the present invention is to extend the residence time on tooth surfaces of various remineralizing ingredients used in various OTC and professional, remineralizing procedures.

A further object of the invention is to improve professional oral care "in-chair" remineralizing procedures.

Yet another object of the invention is to improve remineralizing of children's teeth, while reducing the level of fluoride required for such remineralizing.

Yet still another object of the invention is to reduce the level of fluoride required to effect remineralization of tooth surfaces by extending the residence time of the remineralizing ingredients on tooth surfaces.

Still another object of the invention is to extend the residence time on tooth surfaces of various remineralizing ingredients, while also controlling the rate of release of various remineralizing ingredients onto tooth surfaces.

A still further object of the invention is to dispense remineralizing ingredients on to tooth surfaces in an aqueous-free emulsion such that, when they come in contact with saliva, these ingredients form mucoadhesive gels substantive to tooth surfaces; wherein the mucoadhesive gels are subsequently capable of being solubilized by saliva flow, thereby extending the duration of the remineralizing treatment.

The remineralizing compositions and the treatments of the present invention, as detailed below, are responsive to the objects of the invention.

SUMMARY OF THE INVENTION

The present invention is directed to improved remineralizing compositions and to more effective remineralizing treatments for demineralized tooth surfaces. Active remineralizing ingredients, useful in the compositions of the invention, include: various fluorides, various amorphous calcium, phosphate fluoride mixtures (ACPF), bioglass (NovaMin®), tricalcium phosphate, fluoride mixtures and combinations thereof.

More effective remineralizing treatments of the present invention for demineralized tooth surfaces include various self-applied treatments with dental devices, toothpastes, gels, rinses, chewing gum, lozenges, etc., containing compositions of the present invention; as well as various professional "in-chair" procedures including varnishes, gels, rinses, etc., with professional versions of the compositions of the invention.

The remineralizing compositions of the present invention and remineralizing treatments of the present invention utilize an aqueous-free emulsion containing various remineralizing ingredients, wherein the emulsion in the presence of saliva forms a mucoadhesive gel that is substantive to tooth surfaces. The substantive, mucoadhesive gel slowly dissolves in the presence of saliva, gradually releasing remineralizing ingredients, onto tooth surfaces. This slow release of remineralizing ingredients continues until the mucoadhesive gel is eventually totally solubilized by saliva. This gradual release of remineralizing ingredients from the mucoadhesive gel minimizes the "wash-out" effect of remineralizing ingredients characteristic of commercial remineralizing products and associated commercial treatments presently available.

The resultant "extended" remineralizing feature of the compositions and treatments of the present invention represent a major advance in effective remineralizing, along with reduced risk associated with lower levels of fluoride, required to effect remineralization.

ACP/aqueous-free emulsion compositions and ACPF/aqueous-free emulsion compositions are preferred embodiments of the present invention.

BRIEF DESCRIPTION OF THE DRAWINGS

The substantivity of the aqueous-free emulsion containing active ingredient, in the presence of water, is demonstrated visually by the Drawings included herein, where.

DETAILED DESCRIPTION OF THE PRESENTLY PREFERRED EMBODIMENTS

Aqueous-free emulsions of the present invention that serve as carriers for various remineralizing ingredients are characterized by their ability, in the presence of saliva, to form mucoadhesive gels which are substantive to tooth surfaces. These substantive, mucoadhesive gels of the present invention are further characterized by their ability to: (a) gradually dissolve when exposed to saliva flow, and (b) gradually release various remineralizing ingredients onto tooth surfaces. This gradual dissolution feature of mucoadhesive gels of the present invention minimizes saliva "washout" of remineralizing ingredients by effecting a gradual slow release of remineralizing ingredients onto tooth surfaces. The substantive, mucoadhesive gels of the present invention extend the duration of remineralizing of tooth surfaces under treatment; thereby enhancing the effectiveness of various remineralizing treatments of the present invention, while reducing the level of fluoride required to achieve effective remineralization.

All of the references cited herein, are hereby, in their entirety, incorporated by reference into the present invention.

The Role of ACPF Mixtures in Remineralizing Tooth Surfaces

The remineralizing properties of the preferred amorphous calcium phosphate fluoride mixtures (ACPF) of the present invention are described: by Ming Tung in U.S. Pat. Nos. 5,037,639; 5,268,167; 5,427,768; 5,437,857; 5,460,803; 5,562,895; by Tung in the American Dental Association Foundation publication, "ACP Technology,"; by Schemahorn, et. al., in *The Journal of Clinical Dentistry* Vol. XXII: No 2. 51-54, 2011; and by the 19 references cited by Schemahorn, et. al.

In addition, amorphous calcium phosphate is described by Wikipedia as follows:

"Amorphous calcium phosphate (ACP) is a substance used as a dental treatment. Calcium and phosphate are natural building blocks of teeth, and when present in insufficient amounts, there can be sensitivity after procedures such as dental bleaching or professional dental cleansing. Amorphous calcium phosphate will help in restoring the necessary mineral balance in the mouth in an easy and efficient way.

"ACP technology using a two-phase delivery system that prevents the calcium and phosphate from reacting was developed by Ming S. Tung at the American Dental Research Association's Paffenbarger Research Center. It was first used in a toothpaste called Enamelon in 1999, but it failed commercially. It is now found in Arm & Hammer's Enamel Care Toothpaste (introduced in 2004) as well as their Age Defying Toothpaste, Discus Dental's Nite White bleaching gel, Discus Dental's Relief ACP sensitivity relief product, and Premier Dental's Enamel Pro polishing paste. It is also used in the Aegis product line, such as Aegis® Pit and Fissure Sealant with ACP, produced by the Harry J. Bosworth Company for use by dental professionals. Other Aegis Products include: Aegis® Orthodontic Adhesive with ACP, Aegis® Liner with ACP, Aegis® V with ACP and Aegis® Crown and Bridge with ACP."

According to Ming Tung, after the ACPF salts in the aqueous-free emulsions are dissolved in saliva, they precipitate and hydrolyze to tooth mineral as follows: In an acidic environment, the following reactions occur rapidly; leading to remineralization of tooth surfaces that have been physically cleaned:

The $Ca^{2+}$ and $X^{2+}(HPO_4)^{2-}+F^-$ ions precipitate as $CaF_2Ca_9X(PO_4)_6F_2$ (ACXPF).

Subsequent hydrolysis of this precipitate releases fluoridated tooth mineral:

$$Ca_{10}(PO_4)_6F_2+F^-+(H_{1.5}PO_4)^{1.5-}+OH+X^{24}$$

Preferred ACPF, Aqueous-free emulsions of the present invention, contain:
calcium gluconate,
calcium lactate, gluconate,
disodium hydrogen phosphate,
sodium fluoride, and
citric acid, or ascorbyl palmitate.

The aqueous-free emulsions of the present invention hold the various remineralizing salts in suspension without the salts reacting. When this aqueous-free emulsion is exposed to saliva, it forms a mucoadhesive gel that is substantive to tooth surfaces. This mucoadhesive gel continues to hold the various remineralizing ingredients without the ingredients reacting.

Eventually, this mucoadhesive gel is dissolved by saliva, releasing the unreacted ACPF components onto the hydroxyapatite. The ACPF components penetrate the hydroxyapatite, subsequently forming amorphous calcium phosphate fluoride precipitates within the hydroxyapatite.

Remineralizing, functional, aqueous-free emulsions of the present invention contain stable cations and stable anions, suitable for subsequently reacting to remineralize dental enamel; wherein:

(1) said aqueous-free emulsion inhibits premature reaction of the cations with the anions;

(2) the cations and anions are introduced onto tooth surfaces via saliva soluble, mucoadhesive gels that are substantive to: hydroxyapatite, dentin, biofilm, pellicle, soft tissue, etc.;

(3) the cations and anions are gradually released onto the hydroxyapatite as the saliva soluble, mucoadhesive gels undergo dissolution at rates generally controlled by saliva flow;

(4) local saliva flow can be further controlled by saliva enhancers such as spilanthes extract, which are introduced onto tooth surfaces from said aqueous-free emulsion;

(5) local pH environment for said dissolving gels is controlled, in part, by pH controlling compositions, such as: ascorbyl palmitate, citric acid, etc., present in said aqueous-free emulsion, where the pH controlling composition also assists in substantivity of the various cations and anions released onto tooth surfaces upon dissolution of said mucoadhesive gels;

(6) said saliva soluble gel controls the rate of release of cations onto tooth surfaces, thereby controlling diffusion of said cations into demineralized subsurfaces and/or into dentinal tubules;
(7) said saliva soluble gel also controls rate of release of anions onto tooth surfaces, thereby controlling diffusion of said anions into demineralized subsurfaces and/or into exposed tubules;
(8) said solubilized cations and anions, after diffusing into demineralized subsurfaces and/or into exposed tubules: react and precipitate in an amorphous state remineralizing hydroxyapatite;
(9) said aqueous-free emulsion comprises polydimethylsiloxane, at various molecular weights emulsified in nonionic surfactants comprised of copolymers comprised of polyoxypropylene and polyoxyethylene that form mucoadhesive gels in the presence of saliva; and
(10) said remineralizing, functional, aqueous-free emulsions can be dispensed via: dental tape, dental floss, toothpaste, prophy paste, fluoride varnishes, fluoride gels, dry mouth gels and combinations thereof.

For purposes of the present invention, saliva soluble, aqueous-free emulsions ingredients include those emulsions that are comprised of polydimethylsiloxane in a nonionic surfactant, as described in the following U.S. Pat. Nos. 5,032,387; 5,098,711; 5,538,667 and 5,651,959; all of which are hereby incorporated by reference. Only those aqueous-free emulsions described in the referenced U.S. patents that form mucoadhesive gels substantive to tooth surfaces are useful for purposes of the present invention.

Preferred nonionic surfactants of the present invention capable of forming mucoadhesive gels in the presence of saliva, are selected from the group consisting of: poloxamer 237, poloxamer 338, poloxamer 407 and combinations thereof.

Preferred aqueous-free, saliva soluble emulsions for use in the remineralizing compositions of the present invention include emulsions of polydimethylsiloxane (PDMS) at viscosities ranging from between about 1500 cs and about 2.5 million cs. Particularly preferred, aqueous-free emulsions include as the discontinuous phase PDMS at viscosities between 10,500 cs and 2.5 million cs with those nonionic surfactants described in detail in U.S. Pat. No. 5,651,959 that form mucoadhesive gels in the presence of saliva, as the continuous phase.

Preferred polydimethylsiloxanes are selected from the group consisting of polydimethylsiloxane: at 1500 cs, at 12,500 cs, at 100,000 cs, at 250,000 cs, at 500,000 cs, at 750,000 cs, at 1.5 million cs, at 2.2 million cs, at 2.5 million cs and combinations thereof.

Preferred application means for the remineralizing compositions of the present invention include: oral gels, oral ointments, oral pastes, oral varnishes, toothpastes, oral liquids, lozenges, chewing gums and various interproximal devices coated with said remineralizing compositions.

The present invention is further described and illustrated in examples 1 through 29, which describe certain embodiments of the invention, while also suggesting other uses for the invention.

Examples 1 to 9

Prophy Tape® with Ultramulsion® & ACPF

Example 1

ACPF Prophy Tape®

A 2 gallon stainless steel vessel was fitted with an overhead stirrer and place on a hotplate. An aqueous-free emulsion comprising poloxamer 407/polydimethylsiloxane (12,500 cs) 90:10; 945.63 gm and 1200 gm of poloxamer 407 were placed in the vessel and melted while stirring. The temperature rose to 90 degrees Centigrade and the following ingredients were added: Pluracare L-1220, 120 gm; stearyl alcohol, 450.8 gm; microwax ML445, 267.6 gm; and PEG 8000, 388 gm, were added to the molten aqueous-free emulsion. A homogenizer was placed in the vessel and emulsification resulted from 10 minutes of action. The following ACPF ingredients were then added with stirring: Calcium gluconate, 240 gm; Calcium lactate gluconate, 84 gm; disodium hydrogen phosphate, 48 gm; sodium fluoride, 4.4 gm; propyl gallate, 4 gm; sodium saccharin, 96 gm; EDTA, 8 gm; flavor, 104 gm; and citric acid, 40 gm. The emulsified tape coating batter was then dispensed into the tape coating tank. Compression coating of ultra-high-molecular-weight polyethylene dental tape at 67 mg/yard was completed to give a saliva soluble, coated, dental tape with amorphous calcium phosphate fluoride effects. The tape was overcoated with pumice at between 6 and 10 gm/yd and post-flavored via flavor transfer from a flavor reservoir.

Following the procedures set out in Example 1, PROPHY TAPE® Examples 2 through 9, as detailed in Table 1 below, were prepared. All PROPHY TAPES® were overcoated with pumice abrasive and post-flavored via flavor transfer from a flavor reservoir in a flavor-sealed package.

TABLE 1

ACPF PROPHY TAPE ® EXAMPLES 2 through 9

| | | ACPF Ingredients (all % by wt.) | | | |
|---|---|---|---|---|---|
| Example # | Aqueous-free Emulsion | Gluconate Phosphate | Calcium Lactate | Disodium Hydrogen | Sodium Fluoride |
| 2 | 23.81 | 7.5 | 2.62 | 1.5 | 0.09 |
| 3 | 26.7 | 5 | 1.74 | 1.0 | 0.05 |
| 4 | 11 | 7.5 | 2.62 | 1.5 | 0.138 |
| 5 | 5 | 7.5 | 2.62 | 1.5 | 0.138 |
| 6 | 11 | 5 | 1.74 | 1.0 | 0.09 |
| 7 | 5 | 5 | 1.74 | 1.0 | 0.09 |
| 8 | 11 | 2.5 | 0.873 | 0.5 | 0.05 |
| 9 | 5 | 2.5 | 0.873 | 0.5 | 0.05 |

Illustrative Examples 10 Through 24

Examples summarized in Tables 2 through 4 below, further illustrate the broad range of improved remineralizing compositions, in various dispensing means.

All of the illustrative remineralizing Examples, set out Tables 2 through 4, are to be formulated to form mucoadhesive gels when dispensed in the presence of saliva, which mucoadhesive gels are substantive to tooth surfaces and capable of gradual dissolution upon continuous exposure to saliva.

Following the procedures in Example 1, the aqueous-free emulsion compositions can be prepared and used for coating PROPHY TAPE®, PTFE dental tape and multifilament dental floss, as detailed in Examples 10 through 14 in Table 2 below.

TABLE 2

Illustrative Examples 10 through 14 PROPHY TAPE ®, PTFE Dental Tape, Multifilament Dental Floss

| Example # | Composition of Aqueous-free Emulsion | Remineralization Ingredients (% by wt.) | Saliva Enhancement Ingredient (% by wt.) | Dispensing means |
|---|---|---|---|---|
| 10 | PDMS (2.5 mm cs) 10% in poloxamer 407 at 24% | Bioglass (7.5) | *Spilanthes* Extract (0.6) | Multifilament dental floss with base coating between 40 and 60 mg/yd |
| 11 | PDMS (2.5 mm cs) 20% in poloxamer 407 at 15% | Tricalcium Phosphate (5) Sodium Fluoride (1.1) | *Spilanthes* Extract (0.2) | Multifilament dental floss with base coating between 50 and 70 mg/yd |
| 12 | PDMS (12,500 cs) 20% in poloxamer 407 at 25% | Stannous Fluoride (2.06) | *Spilanthes* Extract (0.15) | PTFE dental tape with base coating between 50 and 70 mg/yd |
| 13 | PDMS (2.5 mm cs) 10% in poloxamer 338 at 25% | Sodium monofluorophosphate (3.78) | *Spilanthes* Extract (0.4) | PROPHY TAPE ® with base coating between 55 and 75 mg/yd |
| 14 | PDMS (2.5 mm cs) 20% in poloxmer 407 at 20% | Sodium fluoride (1.11) | *Spilanthes* extract (0.1) | PROPHY TAPE ® with base coating between 60 and 80 mg/yd |

Following the procedure in Example 1, the remineralizing, aqueous-free emulsion compositions described in Examples 15 through 19 in Table 3 below can be prepared for use in Prophy Pastes, and various alternatives to Prophy Pastes.

TABLE 3

Illustrative Examples 15 through 19

| Example # | Composition of Aqueous free Emulsion (% by wt.) | Remineralization Ingredients (% by wt.) | Saliva Enhancement Ingredient (% wt.) | Dispensing Means |
|---|---|---|---|---|
| 15 | PDMS (2.5 mm cs) 35% in poloxamer 407 at 1% | Bioglass (5) | *Spilanthes* extract (0.4) | prophy paste |
| 16 | PDMS (2.5mm cs) 10% in poloxamer 338 at 3% | tricalcium phosphate (5) and Sodium Fluoride (1.1) | *Spilanthes* extract (0.25) | prophy paste |
| 17 | PDMS (2.5mm cs) 35% in poloxamer 407 1.5% | stannous fluoride (2.1) | *Spilanthes* extract (0.1) | prophy paste |
| 18 | PDMS (2.5 mm cs) 35% in poloxamer 407 at 1% | sodium monofluorophosphate (3.79) | *Spilanthes* extract (0.12) | prophy paste |
| 19 | PDMS (2.5 mm cs) 35% in poloxamer 338 at 1% | sodium fluoride (1.1) | *Spilanthes* extract (0.3) | prophy paste |

Examples 20 Through 24

Following the procedures in Example 1, the aqueous-free emulsion compositions can be prepared and used for toothpaste, as detailed in Example 20 through 25 of Table 4.

TABLE 4

Illustrative Examples 20 through 25

| Example # | Composition of aqueous-free emulsion (% by wt.) | Remineralization ingredients (% by wt.) | Saliva enhancement ingredient (% by wt.) | Dispensing Means |
|---|---|---|---|---|
| 20 | PDMS (2.5 mm cs) 20% in poloxamer 407 3% | Bioglass (6.0) | *Spilanthes* Extract (0.12) | Toothpaste |
| 21 | PDMS (2.5 mm cs) 10% in poloxamer 407 3% | Tricalcium phosphate (5) and Sodium fluoride (1.1) | *Spilanthes* extract (0.1) | Toothpaste |
| 22 | PDMS (2.5 mm cs) 20% in poloxmer 338 2% | Stannous fluoride (2.06) | *Spilanthes* extract (0.2) | Toothpaste |
| 23 | PDMS (2.5 mm cs) 20% in poloxamer 407 2.5% | Sodium monofluorophosphate (3.79) | *Spilanthes* extract (0.25) | Toothpaste |
| 24 | PDMS (2.5 mm cs) 10% in poloxamer 338 2% | Sodium fluoride (1.1) | *Spilanthes* extract (0.1) | Toothpaste |
| 25 | PDMS (2.5 mm cs) 10% in poloxamer 407 2% | ACP (5.0) | *Spilanthes* extract (0.1) | Children's Fluoride-free Tootpaste |

Example 26

Multifilament Dental Floss with ACPF

A 3 gallon stainless steel vessel was fitted with an overhead stirrer and a hot plate. The following ingredients were added with stirring and heating to 90 degrees Centigrade: an aqueous-free emulsion (poloxamer 407, 2673.7 gm; silicone AF1500, 400 gm); sodium saccharin, 92 gm; propyl gallate, 4 gm; silica, 160 gm; sodium fluoride, 5.52 gm; calcium gluconate, 300 gm; calcium lactate gluconate, 104.8 gm; disodium hydrogenphosphate, 60 gm; flavor, 160 gm and citric acid, 40 gm. The vessel was heated and stirred for 20 minutes and the contents transferred to the dental floss applicator tank. Compression coating of the 840 texturized nylon 6,6 yarn produced a dental floss with a coating level of 84 mg/yd. Prior to flossing, the multifilament floss is stretched and released, allowing the texturized floss to expand thereby optimizing interproximal delivery of calcium, phosphate and fluoride to tooth surfaces while leaving a clean just-brushed feeling.

Example 27

Children's Fluoride-Free Toothpaste with ACP/Aqueous-Free Emulsion

A Hobart N-50 mixer fitted with a 1 gallon stainless steel bowl was used to mix the following: PEG 400, 272 gm; an aqueous-free emulsion [poloxamer 407/polydimethyl-siloxane (90:10)], 64 gm; poloxamer 407, 80.8 gm; pluracol L-1220, 80.8 gm; Carbopol 974P, 12 gm; glycerin, 584.8 gm; xylitol powder, 48 gm; acesulfame K, 4.8 gm; titanium dioxide, 16 gm; zeodent, 80 gm; sipernat 22S, 120 gm; perlastin L, 8 gm; sucralose, 2.4 gm; flavor, 28 gm, were stirred for 5 minutes at room temperature. The contents of the bowl were heated to 80 degrees Centigrade. Calcium gluconate, 128 gm; calcium lactate gluconate, 44.8 gm and disodium hydrogenphosphate, 25.6 gm, were then added. After stirring for 10 minutes, the content of the one gallon vessel was transferred to 1.5 oz tubes. Application of 1.5 gram of the toothpaste to the oral mucosa with brushing delivers amorphous calcium phosphate, remineralizing effects; relying on mucoadhesive properties of the gel formed on tooth surfaces in the presence of saliva.

Example 28

Adult Toothpaste with ACPF/Aqueous-Free Emulsion

A Hobart N-50 mixer fitted with a 1 gallon stainless steel bowl was used to mix the following: PEG 400, 272.48 gm; an aqueous-free [poloxamer 407/polydimethyl-siloxane (90:10)], 24 gm; Carbopol 974P, 12 gm; glycerin, 744.96 gm; xylitol powder, 80 gm; acesulfame K, 4.8 gm; titanium dioxide, 16 gm; zeodent 113, 80 gm; sipernat 22S, 120 gm; perlastin L, 16 gm; sucralose, 2.4 gm and flavor, 28.8 gm, were stirred for 5 minutes at room temperature. The contents of the bowl were heated to 80 degrees Centigrade. Calcium gluconate, 128 gm; calcium lactate gluconate, 44.8 gm and disodium hydrogenphosphate, 25.6 gm, were then added. After stirring for 10 minutes, the content of the one gallon vessel was transferred into 2 oz tubes. Application of 2 gram of the toothpaste to the oral mucosa with brushing delivers amorphous calcium phosphate fluoride, remineralizing; relying on the mucoadhesive gel formed on tooth surfaces in the presence of saliva.

Example 29

Comparative Substantivity of Three Toothpastes

An experiment was designed to compare the substantivity properties of three toothpastes. A separate microscope slide was utilized as substrates for each toothpaste. A small bead of toothpaste was applied to a saliva-coated slide. The bead was leveled with a microscope clover slip to obtain a thin coating simulating the thin coat a toothbrush might apply. This procedure was repeated for each of three toothpaste samples. Each slide was immersed in 17 ml of water in a 50 ml beaker. Photographs were taken of side-by-side beakers containing each slide with the thin layer of test toothpaste submerged in water. Photographs at 0, 1, 3, 4, 5, 10, 15 and 20 minutes show the rapid loss of adhesion for the NUPRO® SENSODYNE® toothpaste at one minute and similar loss of adhesion for Clinpro™ 5000 Toothpaste after three minutes. The substantivity of the Children's ACP/ULTRAMULSION® toothpaste to the slide after 20 minutes indicates the substantivity of the mucoadhesive gel that forms in the presence of water or saliva.

The photographs at 0, 1, 3, 4, 5, 10, 15 and 20 minutes are included as FIGS. 1 through 8 of the Drawings.

An Aqueous-Free Emulsion of the Invention Forms a Mucoadhesive Gel

Figure 1:
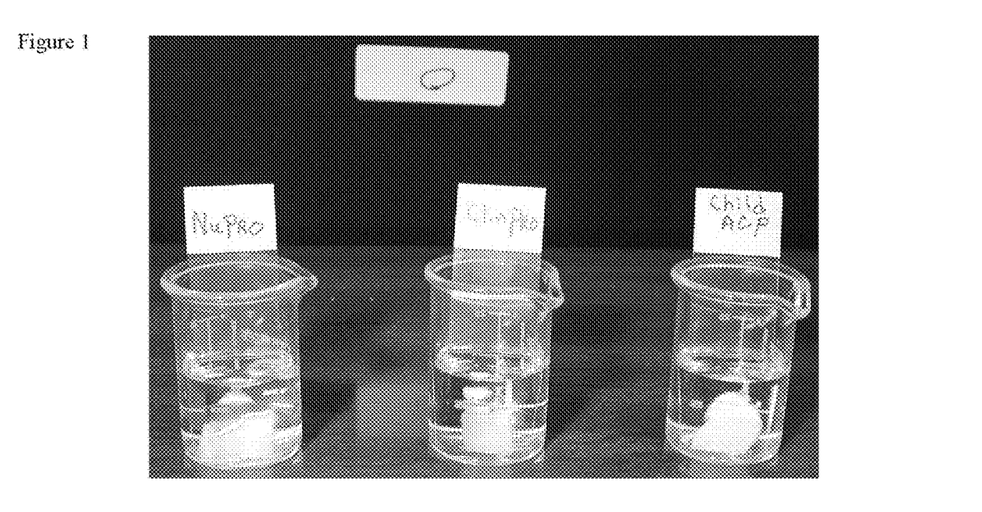
FIGS. 1 through 8 are photographs of three separate microscope slides, each coated with a different remineralizing toothpaste. All three slides are submersed in separate beakers containing water. The photographs indicate various levels of substantivity of the three toothpastes at various time periods.
Figure 2:
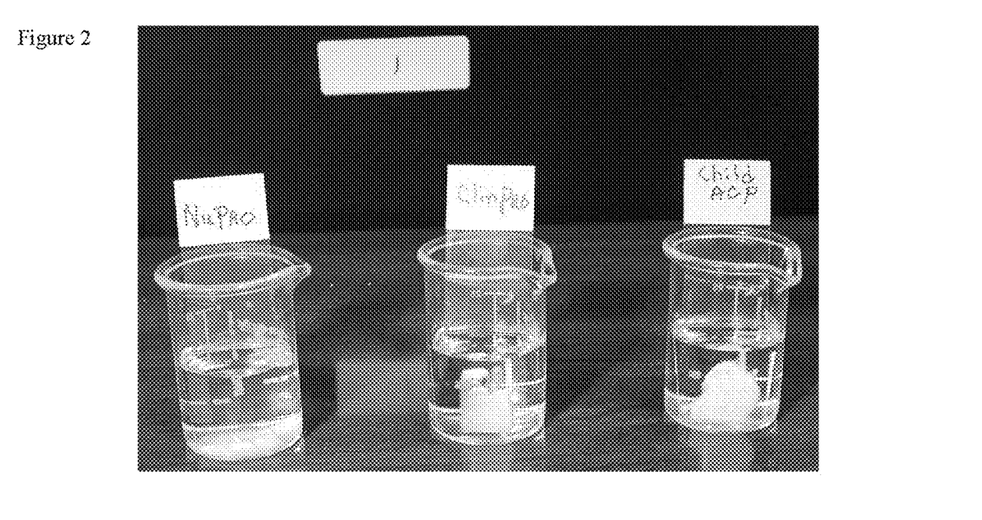
Figure 3:
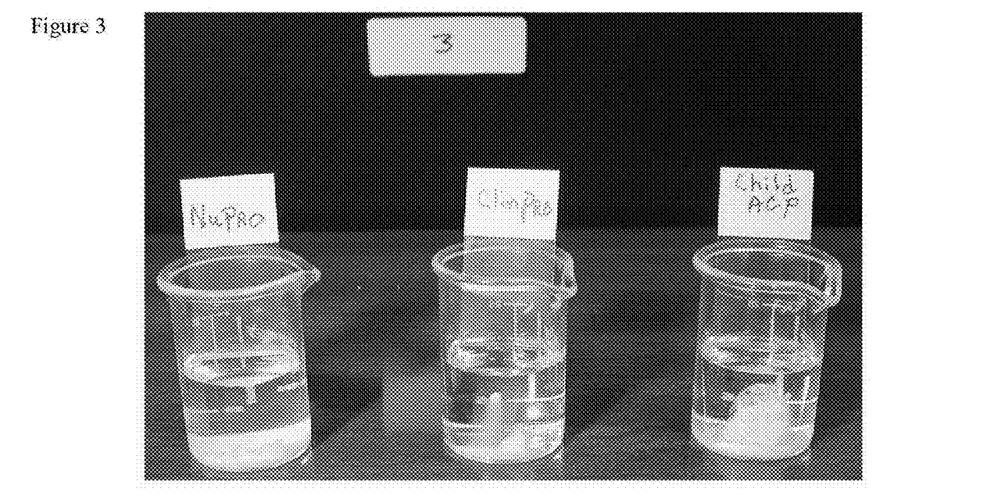
Figure 4:
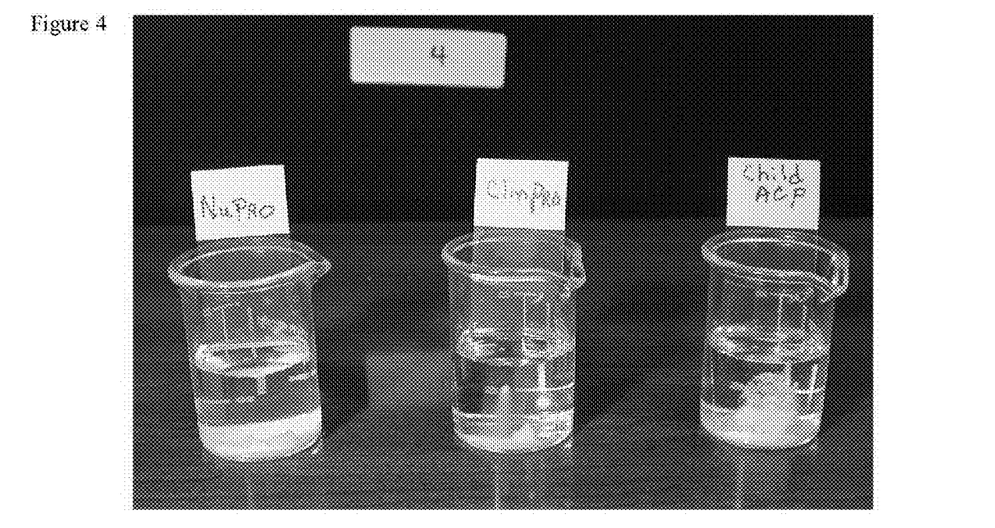
Figure 5:
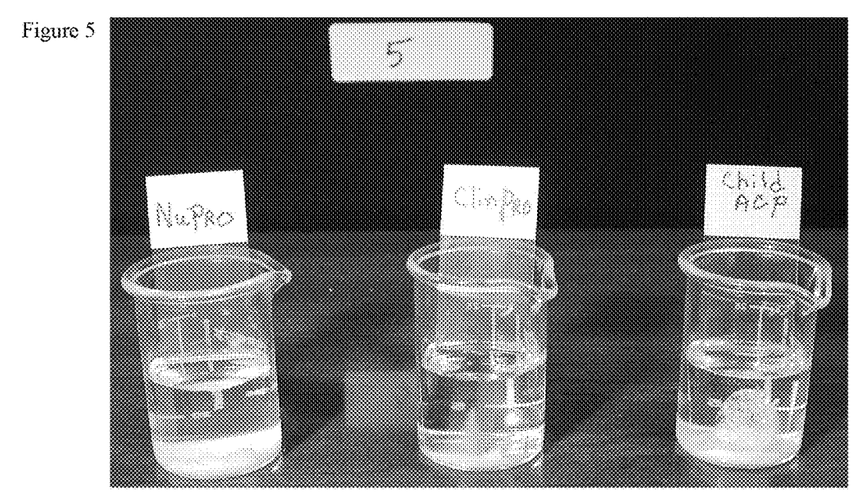
Figure 6:
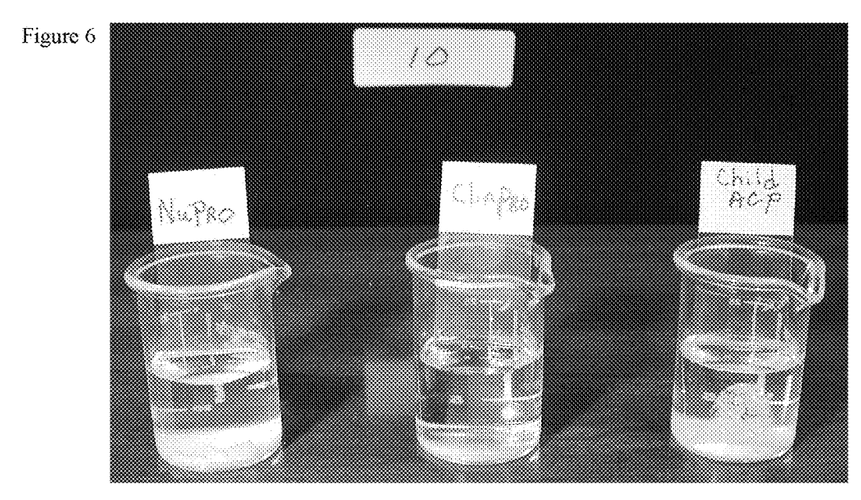
Figure 7:
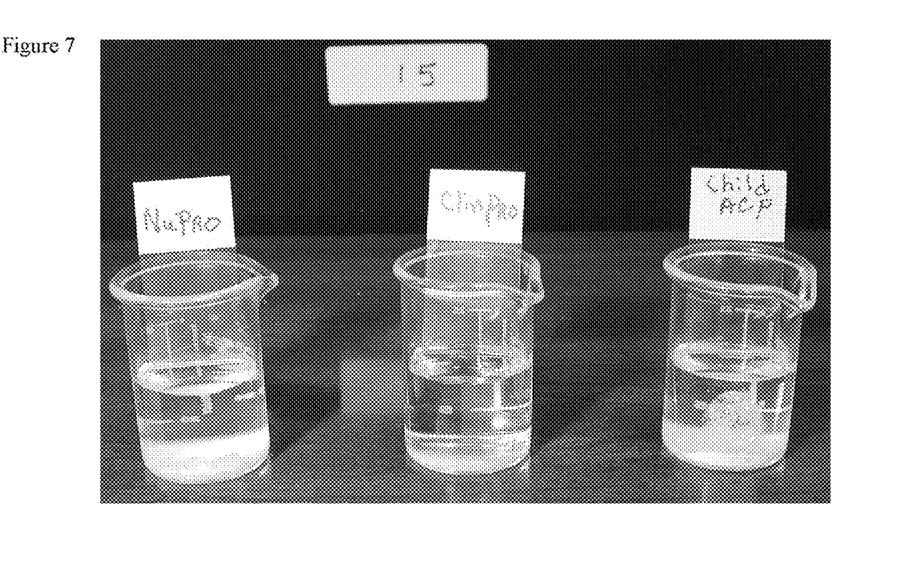
Figure 8:
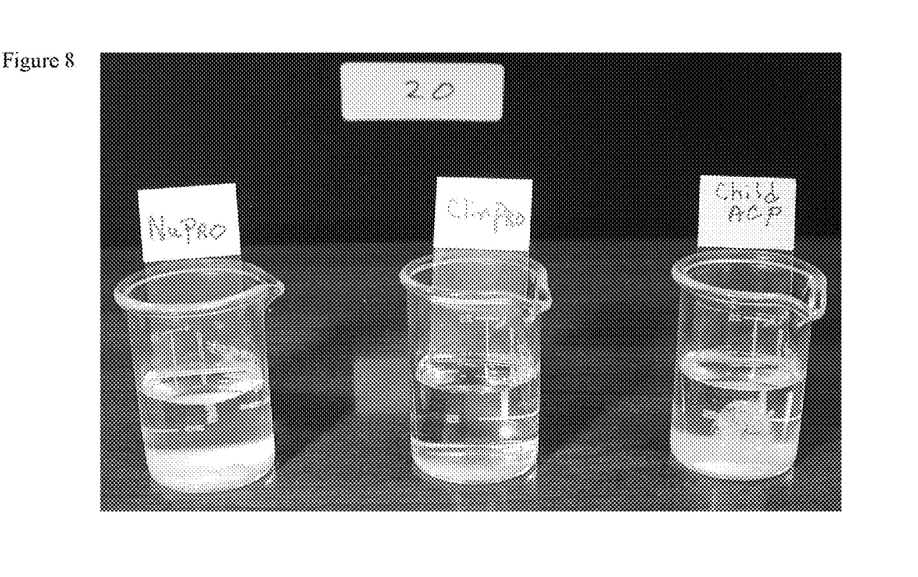
Figure 9:
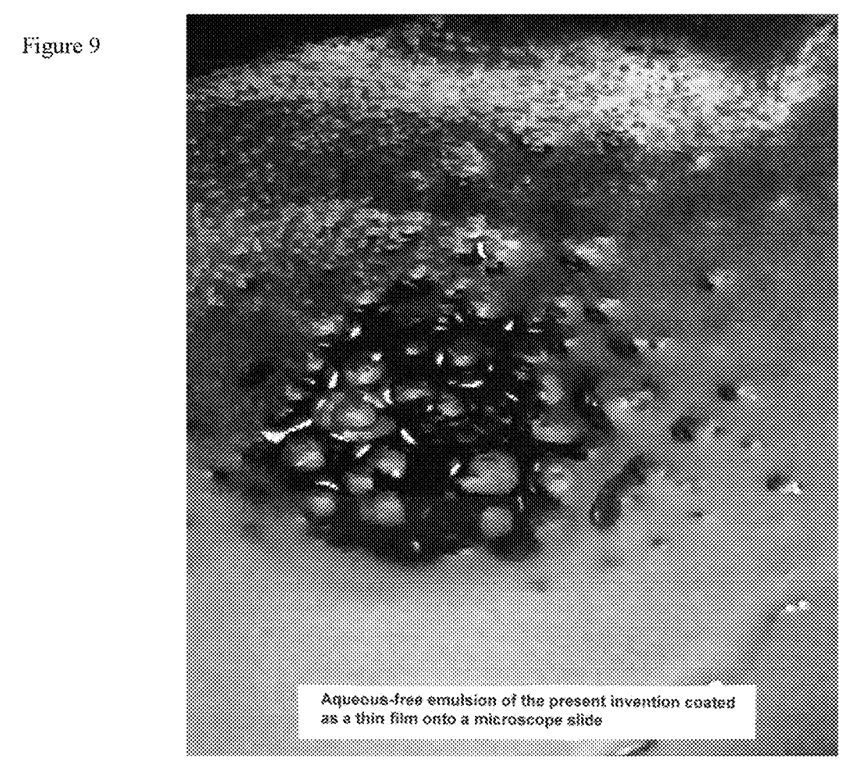
FIGS. 9 through 11 are photographs of a microscope slide coated with an aqueous-free emulsion coating showing conversion of a mucoadhesive gel upon the addition of water.
Figure 10:
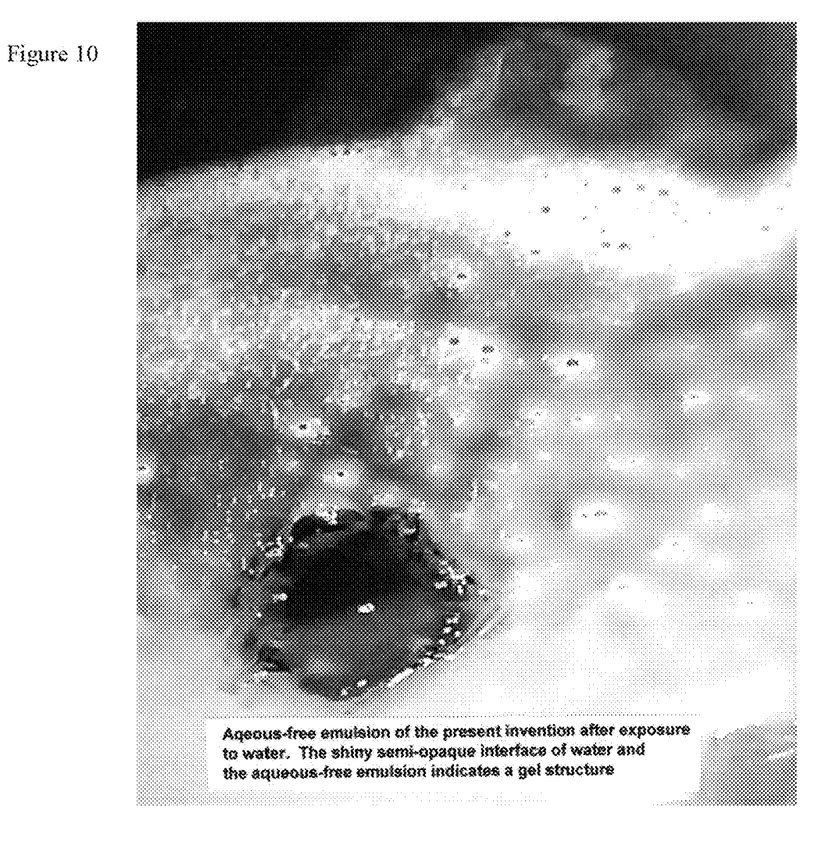
Figure 11:
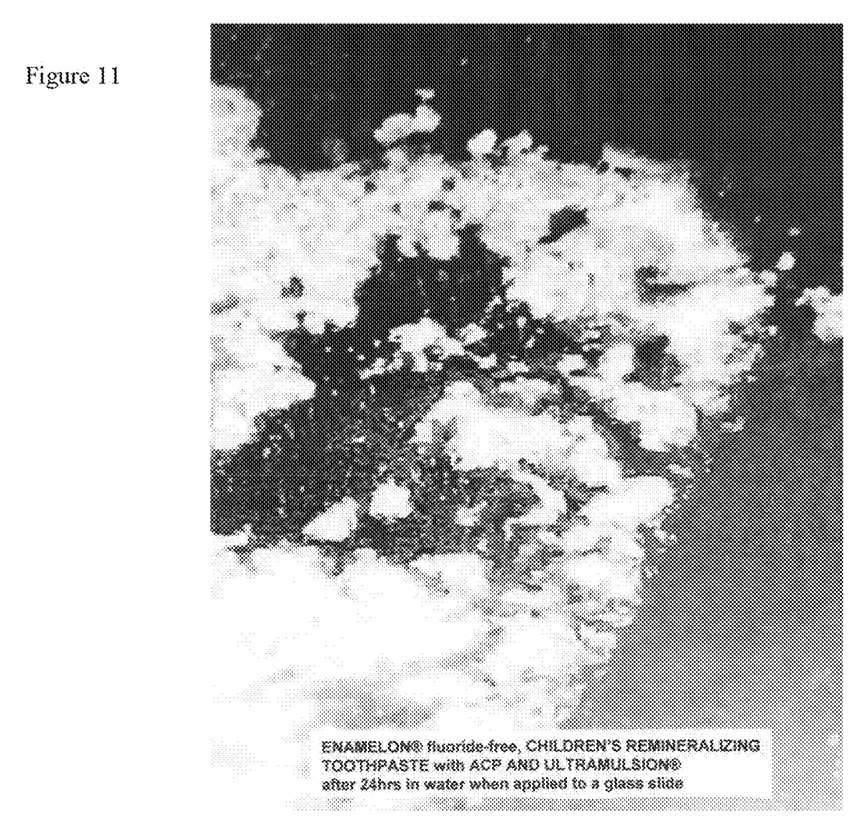

A microscope slide coated with an aqueous-free emulsion of the present invention was treated with water. The photographs of the coated slide before and after application of water are included as FIGS. 9 through 11 of the Drawings.

What is claimed is:

1. A remineralizing and desensitizing composition, comprising an aqueous-free emulsion comprising polydimethylsiloxane as the discontinuous phase and nonionic poloxamer surfactants as the continuous phase and containing remineralizing and desensitizing ingredients of amorphous calcium phosphate fluoride combination, wherein the amorphous calcium phosphate fluoride combination is a combination of calcium gluconate, calcium lactate gluconate, disodium hydrogen phosphate, and fluoride: wherein the pH of said amorphous calcium phosphate fluoride combinations released onto tooth surfaces is adjusted by the addition of pH control compositions selected from the group consisting of: citric acid, ascorbic acid, phosphoric acid, malic acid and combinations thereof; and a saliva flow enhancer selected from the group consisting of Jambu resin, spilanthes extract, spilanthol, and combinations thereof;

wherein said aqueous-free emulsion is present between 5% and 26.7% weight, calcium gluconate between 2.5% and 7.5% weight, calcium lactate gluconate between 0.0873% and 2.62% weight, disodium hydrogen between 0.5% and 1.5% weight, and a fluoride between 0.05% and 0.138% weight, wherein said composition forms a mucoadhesive gel, upon contact with saliva, that is substantive to a tooth surface; wherein said composition comprises a substantivity enhancer selected from the group consisting of: poloxamers, carboxymethyl cellulose, carbopol, gantrez, carrageenan gum, tragacanth gum, xanthan gum, guar gum and combinations thereof, which is present between 0.1% and 0.6% weight; and, wherein said mucoadhesive gel is slowly solubilized upon ongoing contact with saliva, thereby continuously releasing said remineralizing and desensitizing ingredients onto a tooth surface to effect extended remineralization and desensitization of said tooth surface, with a minimum of saliva "wash-out" of said remineralizing and desensitizing ingredients.

2. A remineralizing and desensitizing composition that is substantive to a tooth surface and that extends the duration of remineralization and desensitization treatments comprising: an aqueous-free emulsion comprising polydimethylsiloxane as the discontinuous phase and nonionic poloxamer surfactants as the continuous phase and containing therein amorphous calcium phosphate fluoride as a remineralizing and desensitizing ingredient, wherein said amorphous calcium phosphate fluoride combination is a mixture of: calcium gluconate, calcium lactate gluconate, disodium hydrogen phosphate, and a fluoride component, the composition further comprising a saliva flow enhancer selected from the group consisting of Jambu resin, spilanthes extract, spilanthol, and combinations thereof, and a substantivity enhancer selected from the group consisting of: poloxamers, carboxymethyl cellulose, carbopol, gantrez, carrageenan gum, tragacanth gum, xanthan gum, guar gum and combinations thereof wherein: said aqueous-free emulsion, in the presence of saliva, forms a mucoadhesive gel substantive to said tooth surface, said mucoadhesive gel gradually dissolving in the presence of saliva for releasing onto said tooth surface, said remineralizing and desensitizing ingredients, wherein the pH of said amorphous calcium phosphate fluoride combinations released onto tooth surfaces is adjusted by the addition of pH control compositions selected from the group consisting of: citric acid, ascorbic acid, phosphoric acid, malic acid and combinations thereof; and said remineralizing and desensitizing ingredients continuing to remineralize and desensitize said tooth surface until said substantive mucoadhesive gel is solubilized by said saliva, there by extending the duration of said remineralization and desensitization for effecting improved remineralization and desensitization of said tooth surface, and wherein said aqueous-free emulsion is present between 5% and 26.7% weight, calcium gluconate between 2.5% and 7.5% weight, calcium lactate gluconate between 0.0873% and 2.62% weight, disodium hydrogen between 0.5% and 1.5% weight, and a fluoride between 0.05% and 0.138% weight.

3. A composition according to claim 2, wherein said polydimethylsiloxane discontinuous phase has a viscosity between about 1500 cs and about 2.5 million cs.

4. A composition according to claim 2, wherein said nonionic surfactant continuous phase comprises nonionic surfactants that forms a mucoadhesive gel in the presence of saliva, wherein said gel is substantive to a tooth surface.

5. A composition according to claim 1, wherein means for treating a tooth surface with said composition are selected from the group consisting of: interproximal devices coated with said compositions, prophy paste, varnish, gel, toothpaste, chewing gum, sealant, rinse, and combinations thereof.

6. Improved desensitizing compositions according to claim 1, wherein dispensing means for said improved desensitizing compositions are selected from the group consisting of: interproximal devices coated with said compositions, prophy paste, varnish, gel, toothpaste, chewing gum, sealant, rinse, and combinations thereof.

7. Improved desensitizing compositions according to claim 1, wherein said desensitizing ingredients include commercial versions from the group consisting of: various fluorides, various ACPF mixtures, various bioglass fluoride mixtures, various tricalcium phosphate fluoride mixtures and combinations thereof.

8. Improved, remineralizing, interproximal devices, comprising an aqueous-free emulsion coatings containing remineralizing ingredients; wherein said coating compositions, released during flossing, form mucoadhesive gels, upon contact with saliva, that are substantive to tooth surfaces; and wherein said mucoadhesive gels are slowly solubilized upon ongoing contact with saliva, continuously releasing said remineralizing ingredients onto tooth surfaces to effect extended remineralization of interproximal tooth surfaces, with a minimum of saliva "wash-out" of said remineralizing ingredients,
wherein said aqueous-free emulsion comprises polydimethylsiloxane as the discontinuous phase and nonionic poloxamer surfactants as the continuous phase and contains remineralizing and desensitizing ingredients of amorphous calcium phosphate fluoride combination, wherein the amorphous calcium phosphate fluoride combination is a combination of calcium gluconate, calcium lactate gluconate, disodium hydrogen phosphate, and fluoride: wherein the pH of said amorphous calcium phosphate fluoride combinations released onto tooth surfaces is adjusted by the addition of pH control compositions selected from the group consisting of: citric acid, ascorbic acid, phosphoric acid, malic acid and combinations thereof; and a saliva flow enhancer selected from the group consisting of Jambu resin, spilanthes extract, spilanthol, and combinations thereof;
wherein said aqueous-free emulsion is present between 5% and 26.7% weight, calcium gluconate between 2.5% and 7.5% weight, calcium lactate gluconate between 0.0873% and 2.62% weight, disodium hydrogen between 0.5% and 1.5% weight, and a fluoride between 0.05% and 0.138% weight,
wherein said composition comprises a substantivity enhancer selected from the group consisting of: poloxamers, carboxymethyl cellulose, carbopol, gantrez, carrageenan gum, tragacanth gum, xanthan gum, guar gum and combinations thereof, which is present between 0.1% and 0.6% weight.

9. Improved, remineralizing, interproximal devices containing aqueous-free coating compositions that release during flossing, are substantive to tooth surfaces and that extend the duration of interproximal, remineralizing treatments comprising: an aqueous-free emulsion coating, containing dispensed therein various remineralizing ingredients wherein: said aqueous-free emulsion coating, in the presence of saliva, forms a mucoadhesive gel substantive to said interproximal tooth surfaces, said substantive, mucoadhesive gel gradually dissolves in the presence of saliva, releasing onto said interproximal tooth surfaces, said remineralizing ingredients, and said slowly released remineralizing ingredients continue to remineralize said interproximal tooth surfaces until said substantive mucoadhesive gel is solubilized by said saliva flow, thereby extending the duration of said remineralizing and effecting improved remineralization of said interproximal tooth surfaces,
wherein said aqueous-free emulsion comprises polydimethylsiloxane as the discontinuous phase and nonionic poloxamer surfactants as the continuous phase and contains remineralizing and desensitizing ingredients of amorphous calcium phosphate fluoride combination, wherein the amorphous calcium phosphate fluoride combination is a combination of calcium gluconate, calcium lactate gluconate, disodium hydrogen phosphate, and fluoride: wherein the pH of said amorphous calcium phosphate fluoride combinations released onto tooth surfaces is adjusted by the addition of pH control compositions selected from the group consisting of: citric acid, ascorbic acid, phosphoric acid, malic acid and combinations thereof; and a saliva flow enhancer selected from the group consisting of Jambu resin, spilanthes extract, spilanthol, and combinations thereof;
wherein said aqueous-free emulsion is present between 5% and 26.7% weight, calcium gluconate between 2.5% and 7.5% weight, calcium lactate gluconate between 0.0873% and 2.62% weight, disodium hydrogen between 0.5% and 1.5% weight, and a fluoride between 0.05% and 0.138% weight,
wherein said composition comprises a substantivity enhancer selected from the group consisting of: poloxamers, carboxymethyl cellulose, carbopol, gantrez, carrageenan gum, tragacanth gum, xanthan gum, guar gum and combinations thereof, which is present between 0.1% and 0.6% weight.

10. An improved, remineralizing, interproximal device coating according to claim 9, wherein said polydimethylsiloxane discontinuous phase has a viscosity between about 1500 cs and about 2.5 million cs.

11. An improved, remineralizing, interproximal device coating according to claim 9, wherein said nonionic surfactant is selected from the group consisting of: poloxamers, polysorbates, polyoxyethylene alcohols and combinations thereof.

12. Improved, remineralizing, interproximal device coatings according to claim 8, wherein dispensing means for said improved, remineralizing, interproximal devices are selected from the group consisting of: monofilament, interproximal devices; multifilament, interproximal devices; one-handed flossers, dental stimulators and combinations thereof, coated with said compositions.

13. Improved, remineralizing, interproximal device, coating compositions, according to claim 8; wherein said remineralizing ingredients include commercial versions from the group consisting of: various fluorides, various ACPF mixtures, various bioglass fluoride mixtures, various tricalcium phosphate fluoride mixtures and combinations thereof.

14. Improved, desensitizing, interproximal devices, comprising aqueous-free emulsion coatings containing desensitizing ingredients; wherein said coating compositions are released during flossing and form mucoadhesive gels, upon contact with saliva, that are substantive to tooth surfaces; and wherein said mucoadhesive gels are slowly solubilized upon ongoing contact with saliva, continuously releasing said desensitizing ingredients onto interproximal tooth surfaces to effect extended desensitization of said interproximal tooth surfaces, with a minimum of saliva "wash-out" of said desensitizing ingredients,
   wherein said aqueous-free emulsion comprises polydimethylsiloxane as the discontinuous phase and nonionic poloxamer surfactants as the continuous chase and contains remineralizing and desensitizing ingredients of amorphous calcium phosphate fluoride combination, wherein the amorphous calcium phosphate fluoride combination is a combination of calcium gluconate, calcium lactate gluconate, disodium hydrogen phosphate, and fluoride: wherein the pH of said amorphous calcium phosphate fluoride combinations released onto tooth surfaces is adjusted by the addition of pH control compositions selected from the group consisting of: citric acid, ascorbic acid, phosphoric acid, malic acid and combinations thereof; and a saliva flow enhancer selected from the group consisting of Jambu resin, spilanthes extract, spilanthol, and combinations thereof;
   wherein said aqueous-free emulsion is present between 5% and 26.7% weight, calcium gluconate between 2.5% and 7.5% weight, calcium lactate gluconate between 0.0873% and 2.62% weight, disodium hydrogen between 0.5% and 1.5% weight, and a fluoride between 0.05% and 0.138% weight,
   wherein said composition comprises a substantivity enhancer selected from the group consisting of: poloxamers, carboxymethyl cellulose, carbopol, gantrez, carrageenan gum, tragacanth gum, xanthan gum, guar gum and combinations thereof, which is present between 0.1% and 0.6% weight.

15. Improved, desensitizing, interproximal devices containing aqueous-free, coating compositions that release during flossing, are substantive to interproximal tooth surfaces and that extend the duration of interproximal desensitizing treatments comprising: an aqueous-free, emulsion coating containing dispensed therein various desensitizing ingredients wherein: said aqueous-free, emulsion coating in the presence of saliva, forms a mucoadhesive gel substantive to said interproximal tooth surfaces, said substantive, mucoadhesive gel gradually dissolves in the presence of saliva, releasing onto said interproximal tooth surfaces, said desensitizing ingredients, and said slowly released desensitizing ingredients continue to desensitize said interproximal tooth surfaces until said substantive mucoadhesive gel is solubilized by said saliva flow, thereby extending the duration of said desensitizing and effecting improved desensitization of said interproximal tooth surfaces,
   wherein said aqueous-free emulsion comprises polydimethylsiloxane as the discontinuous phase and nonionic poloxamer surfactants as the continuous phase and contains remineralizing and desensitizing ingredients of amorphous calcium phosphate fluoride combination, wherein the amorphous calcium phosphate fluoride combination is a combination of calcium gluconate, calcium lactate gluconate, disodium hydrogen phosphate, and fluoride: wherein the pH of said amorphous calcium phosphate fluoride combinations released onto tooth surfaces is adjusted by the addition of pH control compositions selected from the group consisting of: citric acid, ascorbic acid, phosphoric acid, malic acid and combinations thereof; and a saliva flow enhancer selected from the group consisting of Jambu resin, spilanthes extract, spilanthol, and combinations thereof;
   wherein said aqueous-free emulsion is present between 5% and 26.7% weight, calcium gluconate between 2.5% and 7.5% weight, calcium lactate gluconate between 0.0873% and 2.62% weight, disodium hydrogen between 0.5% and 1.5% weight, and a fluoride between 0.05% and 0.138% weight,
   wherein said composition comprises a substantivity enhancer selected from the group consisting of: poloxamers, carboxymethyl cellulose, carbopol, gantrez, carrageenan gum, tragacanth gum, xanthan gum, guar gum and combinations thereof, which is present between 0.1% and 0.6% weight.

16. An improved, desensitizing, interproximal device coating according to claim 15, wherein said polydimethylsiloxane discontinuous phase has a viscosity between about 1500 cs and about 2.5 million cs.

17. An improved, desensitizing, interproximal device coating according to claim 15, wherein said nonionic surfactant is selected from the group consisting of: poloxamers, polysorbates, polyoxyethylene alcohols and combinations thereof.

18. Improved desensitizing, interproximal device, coating compositions according to claim 14, wherein dispensing means for said improved desensitizing interproximal devices are selected from the group consisting of: monofilament, interproximal devices; multifilament, interproximal devices; one-handed flossers; dental stimulators and combinations thereof; coated with said compositions.

19. Improved, desensitizing, interproximal device, coating compositions according to claim 15, wherein said desensitizing ingredients include commercial versions from the group consisting of: various fluorides, various ACPF mixtures, various bioglass fluoride mixtures, various tricalcium phosphate fluoride mixtures and combinations thereof.

20. A method for remineralization and desensitization of tooth surfaces, comprising: treating tooth surfaces with an aqueous-free emulsion composition comprising polydimethylsiloxane as the discontinuous phase and nonionic poloxamer surfactants as the continuous phase, and wherein dispensed therein in said aqueous-free emulsion are remineralizing and desensitizing ingredients of amorphous calcium phosphate fluoride combination, wherein the amorphous calcium phosphate fluoride combination is a combination of calcium gluconate, calcium lactate gluconate, disodium hydrogen phosphate, and fluoride; wherein the pH of said amorphous calcium phosphate fluoride combinations released onto tooth surfaces is adjusted by the addition of pH control compositions selected from the group consisting of: citric acid, ascorbic acid, malic acid and combinations thereof; and a saliva flow enhancer selected from the group consisting of Jambu resin, spilanthes extract, spilanthol, and combinations thereof; wherein said aqueous-free emulsion is present between 5% and 26.7% weight, calcium gluconate between 2.5% and 7.5% weight, calcium lactate gluconate between 0.0873% and 2.62% weight, disodium hydrogen between 0.5% and 1.5% weight, and a fluoride between 0.05% and 0.138% weight, wherein said composition forms a mucoadhesive gel, upon contact with saliva, that is substantive to a tooth surface; wherein said composition comprises a substantivity enhancer selected from the group consisting of: poloxamers, carboxymethyl cellulose, carbopol, gantrez, carrageenan gum, tragacanth gum, xanthan gum, guar gum and combinations thereof of between 0.1% and 0.6% weight; and wherein said mucoadhesive gel is slowly solubilized upon ongoing contact with saliva, continuously releasing said remineralizing and desensitizing ingredients onto tooth surfaces to effect extended remineralization and desensitization of said tooth surfaces, with a minimum of saliva "wash-out" of said remineralizing and desensitizing ingredients.

21. A method for remineralization and desensitization of tooth surfaces, comprising: treating tooth surfaces with a composition that is substantive to a tooth surface and that extends the duration of said remineralization and desensitization methods, said composition comprising: an aqueous-free emulsion comprising polydimethylsiloxane as the discontinuous phase and nonionic poloxamer surfactants as the continuous phase, and wherein dispensed therein in said aqueous-free emulsion are remineralizing and desensitizing ingredients of amorphous calcium phosphate fluoride as a remineralizing and desensitizing ingredient, wherein said amorphous calcium phosphate fluoride combination is a combination of: calcium gluconate, calcium lactate gluconate, disodium hydrogen phosphate, a fluoride component, and combinations thereof, and a saliva flow enhancer selected from the group consisting of Jambu resin, spilanthes extract, spilanthol, and combinations thereof, and a substantivity enhancer selected from the group consisting of: poloxamers, carboxymethyl cellulose, carbopol, gantrez, carrageenan gum, tragacanth gum, xanthan gum, guar gum and combinations thereof; and wherein: said aqueous-free emulsion forming a mucoadhesive gel substantive to said tooth surface in the presence of saliva, said substantive, mucoadhesive gel gradually dissolving in the presence of saliva, thereby releasing onto said tooth surfaces said remineralizing and desensitizing ingredients, wherein the pH of said amorphous calcium phosphate fluoride combinations released onto tooth surfaces is adjusted by the addition of pH control compositions selected from the group consisting of: citric acid, ascorbic acid, phosphoric acid, malic acid and combinations thereof; and said released remineralizing and desensitizing ingredients continuing to remineralize and desensitize said tooth surfaces until said substantive mucoadhesive gel is solubilized by said saliva flow, thereby extending the duration of said improved, remineralizing and desensatizing method and effecting improved remineralization and desensitization of said tooth surfaces, an wherein said aqueous-free emulsion is present between 5% and 26.7% weight, calcium gluconate between 2.5% and 7.5% weight, calcium lactate gluconate between 0.0873% and 2.62% weight, disodium hydrogen between 0.5% and 1.5% weight, and a fluoride between 0.05% and 0.138% weight.

22. The method according to claim 21, wherein said polydimethylsiloxane discontinuous phase has a viscosity between about 1500 cs and about 2.5 million cs.

23. The method according to claim 21, wherein said nonionic surfactant continuous phase comprises nonionic surfactants that form a mucoadhesive gel in the presence of saliva, wherein said gel is substantive to a tooth surface.

24. The method according to claim 20, wherein means for treating a tooth surface with said composition are selected from the group consisting of: interproximal devices coated with said compositions, prophy paste, varnish, gel, toothpaste, chewing gum, sealant, rinse, and combinations thereof.

* * * * *